(12) United States Patent
Kim et al.

(10) Patent No.: US 12,185,918 B2
(45) Date of Patent: Jan. 7, 2025

(54) OPERATION APPARATUS HAVING TENSION COMPENSATING MECHANISM OF WIRE FOR STEERING END EFFECTOR

(71) Applicant: KOREA INSTITUTE OF SCIENCE AND TECHNOLOGY, Seoul (KR)

(72) Inventors: Keri Kim, Seoul (KR); Jeongryul Kim, Seoul (KR); Seong Il Kwon, Seoul (KR); Yonghwan Moon, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 592 days.

(21) Appl. No.: 17/477,535

(22) Filed: Sep. 17, 2021

(65) Prior Publication Data

US 2022/0257091 A1 Aug. 18, 2022

(30) Foreign Application Priority Data

Feb. 18, 2021 (KR) .................. 10-2021-0021775

(51) Int. Cl.
*A61B 1/005* (2006.01)
*A61B 17/00* (2006.01)
(Continued)

(52) U.S. Cl.
CPC .......... *A61B 1/0057* (2013.01); *A61B 1/0055* (2013.01); *A61B 2017/00314* (2013.01);
(Continued)

(58) Field of Classification Search
CPC ..... A61B 1/0057; A61B 1/0055; A61B 17/29; A61B 2017/00314; A61B 2017/00327;
(Continued)

(56) References Cited

U.S. PATENT DOCUMENTS

2003/0004460 A1  1/2003  Bedell
2007/0232858 A1* 10/2007  Macnamara ......... A61B 1/0057
                                                600/149
2009/0171161 A1*  7/2009  Ewers ................. A61B 1/0053
                                                600/149

FOREIGN PATENT DOCUMENTS

JP     3938700 B2     6/2007
JP    2015-159844 A   9/2015
(Continued)

OTHER PUBLICATIONS

Berengere Bardou et al., "Design of a telemanipulated system for transluminal surgery," 31st Annual International Conference of the IEEE EMBS Minneapolis, Minnesota, USA, Sep. 2-6, 2009, pp. 5577-5582.

(Continued)

*Primary Examiner* — Gary Jackson
*Assistant Examiner* — Sebastian X Lukjan
(74) *Attorney, Agent, or Firm* — CANTOR COLBURN LLP

(57) ABSTRACT

An operation apparatus for performing an operation by steering an end effector includes a wire which is connected to the end effector to steer the end effector, and a tension compensator which is connected with the wire, wherein in an operating state, the tension compensator changes a shape or position in response to tension of the wire to keep the wire tight, and when the wire is pulled to steer the end effector, the tension compensator is shifted to a lock state in which the shape or position is not changed.

16 Claims, 14 Drawing Sheets

(51) Int. Cl.
*A61B 34/00* (2016.01)
*A61B 17/29* (2006.01)

(52) U.S. Cl.
CPC ..... *A61B 2017/00327* (2013.01); *A61B 17/29* (2013.01); *A61B 2034/715* (2016.02)

(58) Field of Classification Search
CPC .......... A61B 17/2909; A61B 2017/291; A61B 34/71; A61B 2017/2908; A61B 2017/2927; A61B 1/0052; A61B 1/0062; A61B 17/00234; A61B 2017/00309; A61B 2017/00323; A61B 2017/0069; A61B 2017/2923
See application file for complete search history.

(56) References Cited

FOREIGN PATENT DOCUMENTS

| | | |
|---|---|---|
| JP | 6153484 B2 | 6/2017 |
| KR | 10-2009-0051049 A | 5/2009 |
| KR | 10-2012-0081913 A | 7/2012 |
| KR | 10-2015-0082243 A | 7/2015 |
| WO | 2008/020964 A2 | 2/2008 |
| WO | 2014/070980 A1 | 5/2014 |

OTHER PUBLICATIONS

Katherine E. Riojas et al., "A Hand-Held Non-Robotic Surgical Tool With a Wrist and an Elbow," IEEE Transactions on Biomedical Engineering, Nov. 2019, pp. 3176-3184, vol. 66, No. 11.

* cited by examiner

OPERATION APPARATUS HAVING TENSION COMPENSATING MECHANISM OF WIRE FOR STEERING END EFFECTOR

CROSS-REFERENCE TO RELATED APPLICATION

This application claims a priority of Korean Patent Application No. 10-2021-0021775, filed on Feb. 18, 2021, and all the benefits accruing therefrom under 35 U.S.C. § 119, the contents of which in their entirety are herein incorporated by reference.

TECHNICAL FIELD

The present disclosure relates to an operation apparatus for performing a predetermined operation by steering an end effector using a wire, and more particularly, to an operation apparatus having a tension compensating mechanism of a wire for steering an end effector.

DESCRIPTION ABOUT NATIONAL RESEARCH AND DEVELOPMENT SUPPORT

This research is conducted by Hanyang Digitech, and funded by robotics industry technology development (R&D) of Korea Evaluation Institute of Industrial Technology, Ministry of Trade, Industry and Energy, Republic of Korea (Development of flexible joint single passage surgical robotic technology based on fluoroscopy-induced endoscopy for transoral and laparoscopic surgery, No. 1415167846).

BACKGROUND ART

A typical example of an operation apparatus for performing a predetermined operation by steering an end effector is a surgical instrument for minimally invasive surgery.

The minimally invasive surgery is a surgery performed with minimal small incisions as opposed to open surgery, and has advantages of reduced scars or aftereffect and fast recovery.

Since surgical instruments for minimally invasive surgery enter the narrow lumen in the body to perform a predetermined operation such as a surgery, in many instances, an end effector capable of changing the direction is installed at the front end of an elongated tube, and a surgical tool is installed at the front end of the end effector.

According to the conventional art, a wire driven apparatus using wires connected to the end effector is widely used to steer the direction of the end effector connected to the front end of the elongated tube.

Among the wire driven apparatuses, an automated apparatus that pulls the wires using a variety of motors involves complicated configuration and intricate control and is high-priced. Accordingly, manually operated surgical instruments that allow an operator himself/herself to manipulate a manipulator, for example, a handle, are widespread.

FIGS. 1 and 2 are schematic diagrams showing the configuration of a manually operated surgical instrument (an operation apparatus) 1 according to the conventional art.

As shown in FIG. 1, the operation apparatus 1 includes a fixture 4 fixed to a holder for fixed placement, a tube 3 extending from the front end of the fixture 4, and an end effector 2 connected to the front end of the tube 3. Additionally, a manipulator 5 is connected to the rear end of the fixture 4 rotatably with respect to the fixture 4.

Two wires 6, 7 connected to the tip of the end effector 2 are connected to the manipulator 5 through the tube 3 and the fixture 4. In general, four wires are connected for 3-dimensional (3D) steering of the end effector, but for convenience of description, only the two wires 6, 7 are illustrated and described herein.

When the end effector 2 is not steered, the two wires 6, 7 are kept tight with the same tension.

For example, to steer the end effector 2 in the clockwise direction in FIG. 2, the operator rotates the manipulator 5 in the clockwise direction. Accordingly, the wire 6 is pulled back and the tip of the end effector 2 is pulled by the wire 6, and thus the tip of the end effector 2 is steered in the clockwise direction. On the contrary, when the operator rotates the manipulator 5 in the counterclockwise direction, the wire 7 is pulled and the tip of the end effector 2 is steered in the counterclockwise direction.

However, as shown in FIG. 2, when the manipulator 5 is rotated in the clockwise direction, the wire 6 is kept tight, but the tension of the wire 7 positioned opposite the wire 6 reduces, and thus the wire 7 is not kept tight and becomes loose.

Of course, the end effector 2 is steered in the clockwise direction and pulls the wire 7 a little bit forwards, but since the length of the end effector 2 is very small compared to the total length of the operation apparatus 1, it is insufficient to keep the wire 7 tight.

In the state of FIG. 2, even though the operator rotates the manipulator 5 in the counterclockwise direction to steer the end effector 2 in the counterclockwise direction, the wire 7 is loose, so the end effector 2 cannot rotate until the wire 7 is pulled tightly. In other words, only after the loose wire 7 is pulled tightly, the end effector 2 is steered.

In spite of the operator's manipulation of the manipulator 5 in the counterclockwise direction, delayed steering of the end effector 2, known as [backlash] occurs due to the loose wire 7.

Likewise, when the flexible tube 3 enters the curved lumen, the tube 3 bends, and the wire on the bent side of the tube 3 may become loose. Additionally, due to the frequent use, the wire itself stretches and becomes loose by fatigue.

In any case, when the wire becomes loose and is not kept tight, the steering of the end effector 2 is not immediately accomplished as desired, resulting in a significant reduction in operational precision of the operation apparatus 1.

The problem caused by the loosening of the wire may occur in not only a manually operated apparatus driven by the operator's manipulation, but also an automated apparatus that pulls wires using a variety of motors.

RELATED LITERATURES

Patent Literatures (Patent Literature 1) US 2003/0004460

DISCLOSURE

Technical Problem

The present disclosure is designed to solve the above-described problem of the conventional art, and therefore the present disclosure is directed to providing an operation apparatus capable of maintaining a precise operation by preventing a wire for steering an end effector from getting loose.

Technical Solution

To achieve the above-described object, according to an aspect of the present disclosure, there is provided an operation apparatus for performing an operation by steering an end effector, the operation apparatus including a wire which is connected to the end effector to steer the end effector, and a tension compensator which is connected with the wire, wherein in an operating state, the tension compensator changes a shape or position in response to tension of the wire to keep the wire tight, and when the wire is pulled to steer the end effector, the tension compensator is shifted to a lock state in which the shape or position is not changed.

According to an embodiment, the tension compensator is formed in contact with the wire on a side of the wire, and changes the shape or position in response to a compression force of the wire.

According to an embodiment, the operation apparatus includes a manipulation shaft which is rotatably formed around a rotation central axis perpendicular to a plane on which a steering trajectory of the end effector is placed, and pulls the wire back, and the tension compensator is spontaneously shifted between the operating state and the lock state by the rotation of the manipulation shaft.

According to an embodiment, the operation apparatus includes a compensation module rotatably formed around the rotation central axis, the compensation module through which the manipulation shaft passes, the tension compensator is fixed to the compensation module movably to change the position, when the manipulation shaft rotates in a direction and comes into contact with the tension compensator, the tension compensator is brought into the lock state, and when the manipulation shaft in contact with the tension compensator continuously rotates in the direction, the manipulation shaft and the compensation module rotate together and pull the wire back.

According to an embodiment, when the manipulation shaft rotates in an opposite direction opposite to the direction on the plane, the manipulation shaft and the tension compensator are released from the contact and the tension compensator is brought into the operating state in which the position changes in response to the tension of the wire.

According to an embodiment, each of the manipulation shaft and the tension compensator has a gear, the gears are engaged with each other on a surface of the contact between the manipulation shaft and the tension compensator, and when the manipulation shaft and the tension compensator come into contact with each other, the gears are engaged with each other, and the tension compensator is brought into the lock state.

According to an embodiment, the tension compensator is connected to the compensation module by an elastic member which is compressed or stretched depending on the tension of the wire.

According to an embodiment, when arbitrary x, y and z axes perpendicular to one another are defined, the operation apparatus includes a first wire for steering the end effector in a clockwise direction on an x-z plane, a second wire for steering the end effector in a counterclockwise direction on the x-z plane, a first tension compensator which is connected to the first wire, and a second tension compensator which is connected to the second wire, when the end effector is steered in the clockwise direction on the x-z plane, the first tension compensator is brought into the lock state, and the second tension compensator is brought into the operating state in which the position changes in response to the tension of the second wire, and when the end effector is steered in the counterclockwise direction on the x-z plane, the second tension compensator is brought into the lock state, and the first tension compensator is brought into the operating state in which the position changes in response to the tension of the first wire.

According to an embodiment, the operation apparatus includes a manipulation shaft rotatably formed around a y-axial rotation central axis, and a compensation module rotatably formed around the y-axis rotation central axis, the compensation module through which the manipulation shaft passes, each of the first tension compensator and the second tension compensator is fixed to the compensation module movably to change the position, and the first tension compensator and the second tension compensator are spontaneously and selectively shifted to the lock state or the operating state depending on a direction of rotation of the manipulation shaft relative to the compensation module.

According to an embodiment, the manipulation shaft is in non-contact with the first tension compensator and the second tension compensator in a neutral state in which the manipulation shaft does not rotate relative to the compensation module.

According to an embodiment, the operation apparatus includes a third wire for steering the end effector in the clockwise direction on an x-y plane, a fourth wire for steering the end effector in the counterclockwise direction on the x-y plane, a third tension compensator which is fixed to the compensation module movably to change the position, and connected to the third wire, and a fourth tension compensator which is fixed to the compensation module movably to change the position, and connected to the fourth wire, the manipulation shaft is rotatably formed around a z-axial rotation central axis, the compensation module is rotatably formed around the z-axial rotation central axis, when the end effector is steered in the clockwise direction on the x-y plane, the third tension compensator is brought into the lock state, and the fourth tension compensator is brought into the operating state in which the position changes in response to the tension of the fourth wire, and when the end effector is steered in the counterclockwise direction on the x-y plane, the fourth tension compensator is brought into the lock state, and the third tension compensator is brought into the operating state in which the position changes in response to the tension of the third wire.

According to an embodiment, 3-dimensional (3D) steering of the end effector is accomplished by 3D manipulation whereby the manipulation shaft simultaneously makes a rotating motion around the y-axial rotation central axis and a rotating motion around the z-axial rotation central axis, and the first tension compensator and the second tension compensator are selectively operated by rotation of x-z plane components during the 3D rotation of the manipulation shaft, and the third tension compensator and the fourth tension compensator are selectively operated by rotation of x-y plane components during the 3D rotation of the manipulation shaft.

According to an embodiment, the operation apparatus includes a first universal joint to allow the compensation module to simultaneously make a rotating motion around the y-axial rotation central axis and a rotating motion around the z-axial rotation central axis, and a second universal joint to allow the manipulation shaft to simultaneously make the rotating motion around the y-axial rotation central axis and the rotating motion around the z-axial rotation central axis.

According to an embodiment, a rotary damper is installed at the first universal joint to give a predetermined rotation resistance for a member coupled to an axis of the first universal joint.

According to an embodiment, the operation apparatus includes a tube having a front end to which the end effector is coupled, the tube through which the wire connected to the end effector passes, and at least a portion of the tube is formed of a flexible material capable of bending.

According to an embodiment, the operation apparatus includes a manipulation shaft rotatably formed around a rotation central axis perpendicular to a plane on which a steering trajectory of the end effector is placed, and a handle coupled to a rear end of the manipulation shaft to allow a user to hold, and the operation apparatus is a non-powered manually operated apparatus which operates by the user who holds the handle and rotates the manipulation shaft.

According to an embodiment, the operation apparatus is a surgical instrument including a surgical tool which is coupled to a front end of the end effector.

BEST MODE

Figure 1:
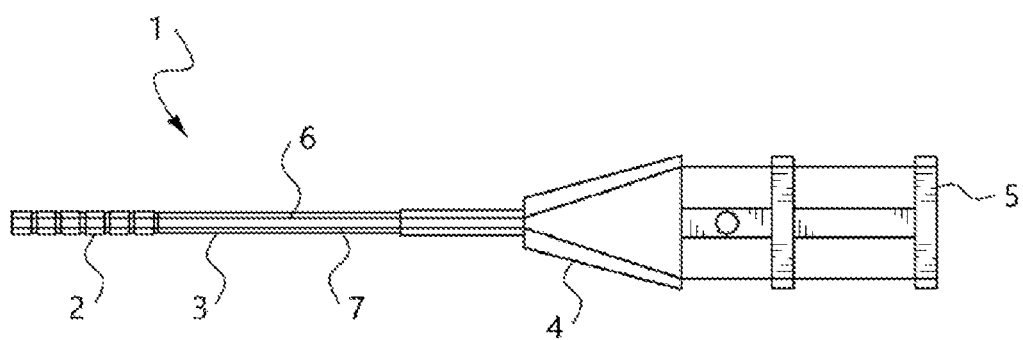
FIGS. 1 and 2 are schematic diagrams showing the configuration of an operation apparatus according to the conventional art.
Figure 2:
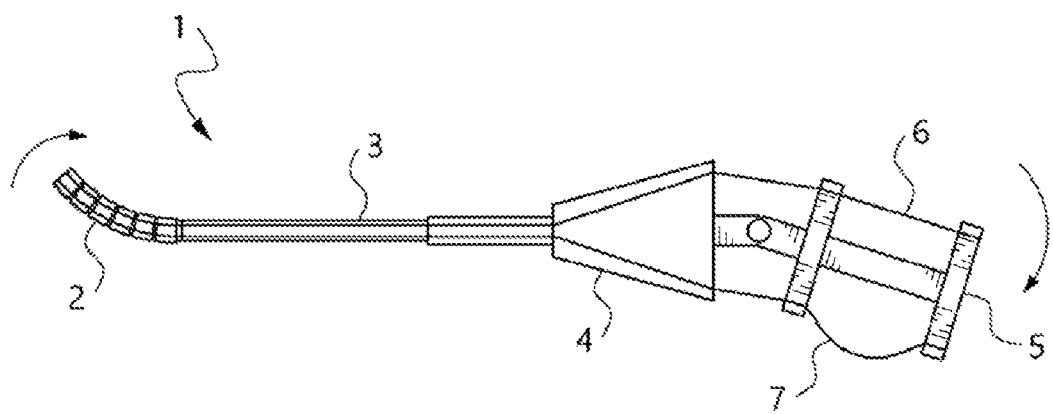

Hereinafter, the preferred embodiments will be described with reference to the accompanying drawings. The present disclosure is described with reference to the embodiments shown in the drawings, but this is just described as an embodiment, and the technical spirit of the present disclosure and the main structure and operation are not limited thereby.

Figure 3:
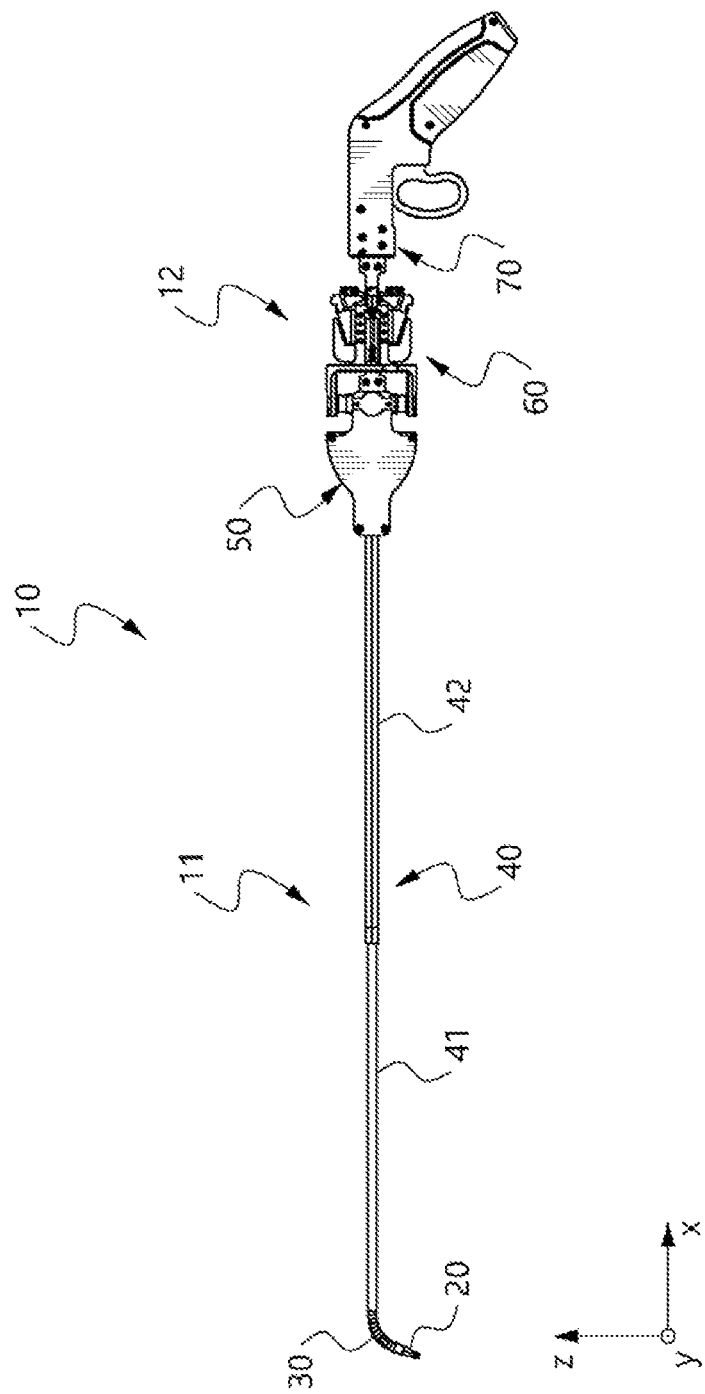
FIG. 3 is a side view of an operation apparatus according to an embodiment of the present disclosure.

FIG. 3 is a side view of an operation apparatus 10 according to an embodiment of the present disclosure.

In some drawings including FIG. 3, x, y and z axes perpendicular to one another are indicated. The x-y-z coordinate system by the x, y and z axes defined in the specification, drawings and claims is not an absolute coordinate system, but an arbitrary coordinate system for describing the steering direction of an end effector 30 and a positional relationship between the elements of the operation apparatus 10. A plane defined by the x and y axes is referred to as an x-y plane, a plane defined by the x and z axes as an x-z plane, and a plane defined by the y and z axes as a y-z plane. Hereinafter, the lengthwise direction of the end effector 30 (the substantial lengthwise direction of the entire operation apparatus 10) is described as being parallel to the x axis.

The operation apparatus 10 according to this embodiment is a surgical instrument for minimally invasive surgery, and is a non-powered manually operated apparatus driven by an operator's manipulation without power. However, the operation apparatus 10 is not necessarily limited to the surgical instrument. Any apparatus for performing a predetermined operation by steering the end effector 30 using a wire may be the operation apparatus of the present disclosure. Additionally, the operation apparatus 10 does not need to be a non-powered manually operated apparatus, and may be a partially automated apparatus using power or a fully automated apparatus.

As shown in FIG. 3, the operation apparatus 10 includes an insertion unit 11 that is inserted into the body, and a manipulation unit 12 to manipulate the end effector 30 and a surgical tool 20 outside the body.

The insertion unit 11 includes the surgical tool 20, the end effector 30 and a tube 40 in a sequential order from the front end. The manipulation unit 12 includes a fixture 50 to which the tube 40 is fixed, an actuation unit 60 and a handle 70.

Figure 4:
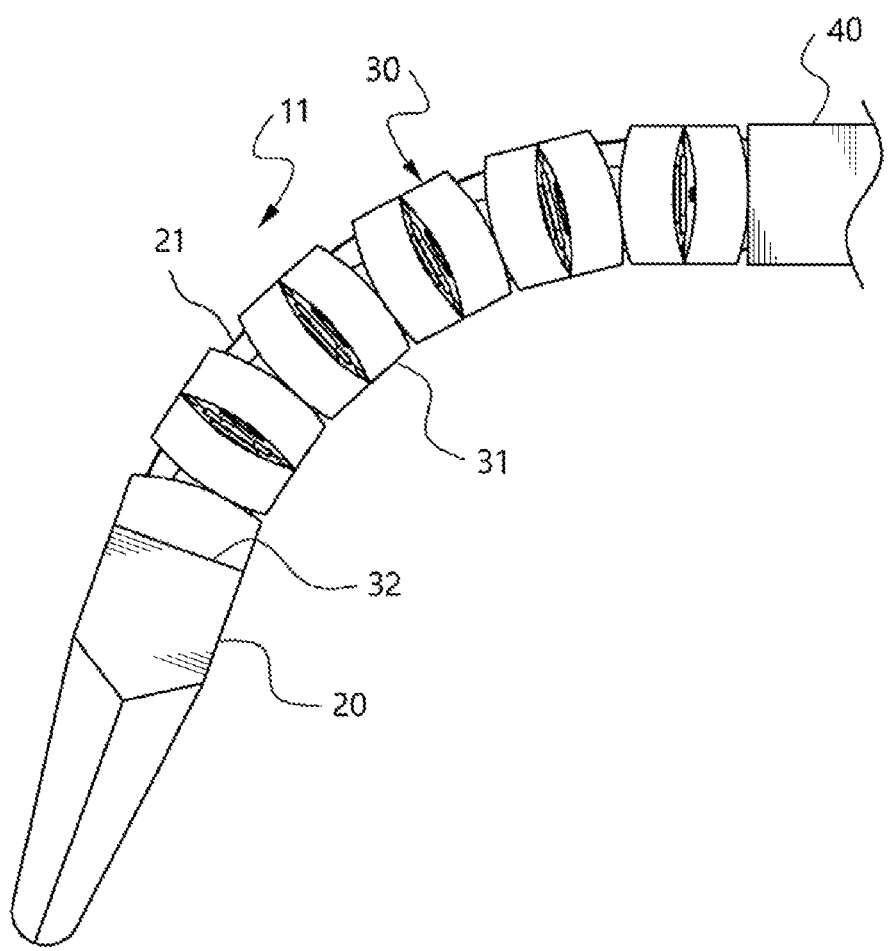
FIG. 4 is an enlarged diagram of an insertion unit of the operation apparatus of FIG. 3.

FIG. 4 is an enlarged diagram of the insertion unit 11 of the operation apparatus 10.

Referring to FIG. 4, the end effector 30 according to this embodiment is a series segment type structure that bends in whole, including a plurality of segments 31 connected in a line, each segment 31 being rotatable relative to each other. The end effector 30 bends in whole by the relative rotation of each segment 31 to steer the direction of a tip 32. The end effector 30 is bendable in three dimensions (3D) to steer the direction of the tip 32 in 3D.

To help the understanding, FIGS. 3 and 4 show the end effector 30 in bent state, but in the initial unsteered state of the end effector 30, each segment 31 is aligned in line and the end effector 30 is in unbent state.

The plurality of segments 31 according to this embodiment is rotatable relative to each other by a rolling motion, but is not limited thereto. For example, the plurality of segments 31 may be connected by pin coupling. Additionally, the end effector 30 is not necessarily limited to the structure including the plurality of segments and may be a single body that is rotatable with respect to the tube 40.

The surgical tool 20 is coupled to the tip 32 of the end effector 30. The surgical tool 20 according to this embodiment is scissors used to cut the tissues. The surgical tool 20 may be a different type of tool, for example, a laser irradiator and forceps, according to the task or the purpose of use of the operation apparatus 10. Additionally, the surgical tool 20 may be detachably coupled to the end effector 30 and may be replaced with a different type of tool when needed.

Referring back to FIG. 3, the tube 40 according to this embodiment includes a rigid part 42 having no flexibility extending from the fixture 50, and a flexible part 41 having flexibility extending from the rigid part 42. When at least a portion of the tube 40 is made of a flexible material that can be bent, the tube 40 may be properly inserted along the curved lumen in the body. The length of the rigid part 42 and the flexible part 41 may be adjusted to conform to the shape of the lumen in the body for entry into the surgery site. Additionally, the entire tube 40 may be formed as the flexible part or the rigid part when needed.

Figure 5:
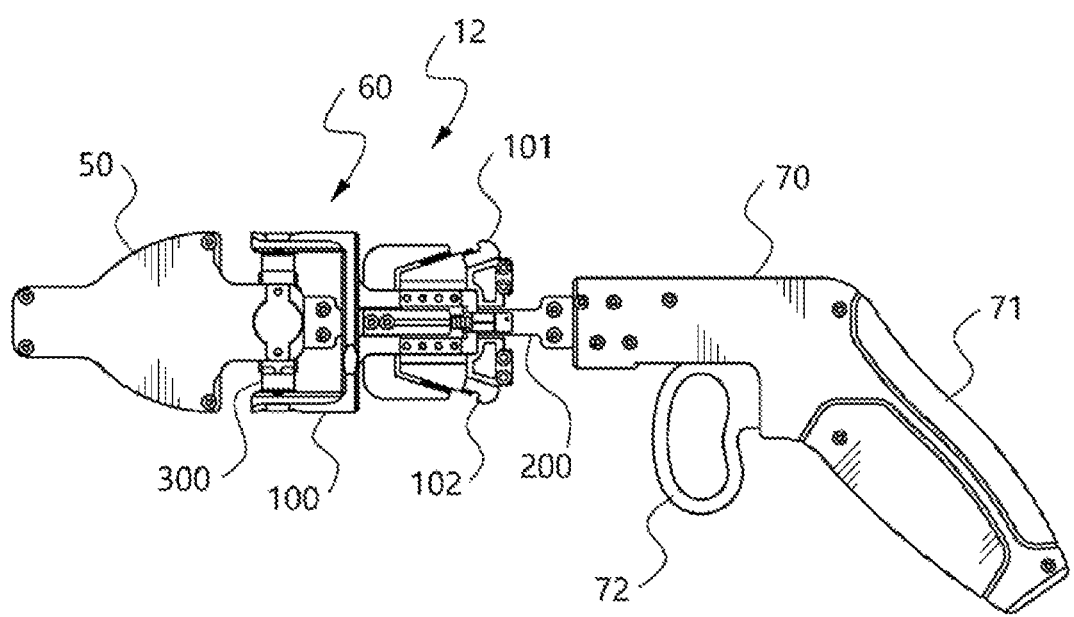
FIG. 5 is an enlarged diagram of a manipulation unit of the operation apparatus of FIG. 3.

FIG. 5 is an enlarged diagram of the manipulation unit 12 of the operation apparatus 10.

The fixture 50 is configured to fix the operation apparatus 10 in a proper position. The fixture 50 is held or fixed to a frame to fix the position and serves as a reference point of motion of the actuation unit 60 or the insertion unit 11.

As shown in FIG. 5, the actuation unit 60 of the manipulation unit 12 includes a joint module 300 connected to the fixture 50, and a compensation module 100 and a manipulation shaft 200 rotatably connected to the fixture 50 by the joint module 300.

Figure 14:
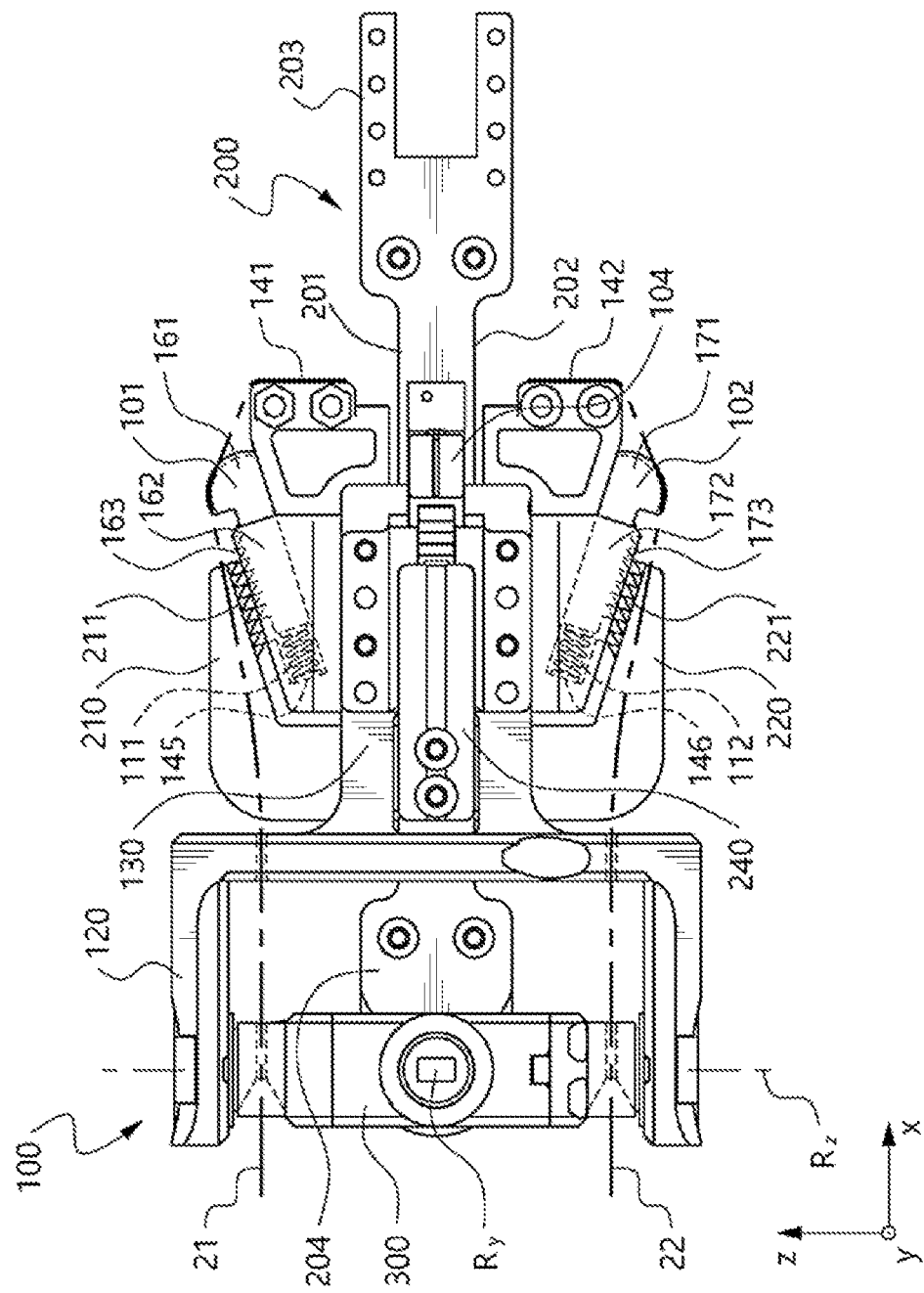

Although not shown in FIGS. 3 and 5, the operation apparatus 10 includes four wires 21, 22, 23, 24 (see FIG. 14). The four wires 21, 22, 23, 24 extend through the end effector 30, the tube 40 and the fixture 50 with their front ends fixed to the tip 32 of the end effector 30. According to this embodiment, the rear ends of the four wires 21, 22, 23, 24 are connected to the compensation module 100.

The compensation module 100 according to this embodiment includes tension compensators 101, 102 to keep the wires tight.

Hereinafter, the operation and function of the tension compensators 101, 102 will be described with reference to FIGS. 6 to 9.

FIGS. 6 to 9 are schematic diagrams showing the configuration of the operation apparatus 10. The detailed configuration of the operation apparatus 10 will be provided below. The surgical tool 20 and the handle 70 are omitted in FIGS. 6 to 9.

As described below, 3D steering of the end effector 30 is possible, but the steering trajectory formed by the tip 32 of the end effector 30 on the x-z plane will be first described herein.

As shown in FIGS. 6 to 9, the operation apparatus 10 includes a first wire 21 to steer the end effector 30 in the clockwise direction on the x-z plane, and a second wire 22 to steer the end effector 30 in the counterclockwise direction on the x-z plane.

The first wire 21 and the second wire 22 are spaced apart in the z direction with respect to the lengthwise central axis of the end effector 30, and extend along the lengthwise direction of the end effector 30. The first wire 21 and the second wire 22 extend through the end effector 30, the tube 40 and the fixture 50 with their front ends fixed to the tip 32 of the end effector 30.

For convenience for illustration, it appears as if the rear ends of the first wire 21 and the second wire 22 are fixed to the manipulation shaft 200 in FIGS. 6 to 9, but in this embodiment, the rear ends of the first wire 21 and the second wire 22 are connected to the compensation module 100. However, the rear ends of the first wire 21 and the second wire 22 may be fixed to the manipulation shaft 200 as shown in FIGS. 6 to 9.

The manipulation shaft 200 is connected to the fixture 50 rotatably around a y-axial rotation central axis Ry perpendicular to the x-z plane on which the steering trajectory of the end effector 30 is placed.

The first tension compensator 101 and the second tension compensator 102 can change the position by moving forward away from the manipulation shaft 200 or moving back close to the manipulation shaft 200.

The first tension compensator 101 is placed facing the first wire 21 and connected to the first wire 21. In the specification, "connection" of two elements includes direct connection to bring the corresponding elements into operation, as well as indirect connection or contact to bring the corresponding elements into operation.

According to this embodiment, the first tension compensator 101 is formed in contact with the first wire 21 on the side of the first wire 21. A first spring 111 which is an elastic member is connected to the first tension compensator 101. The first spring 111 provides the first tension compensator 101 with a pushing force on the first wire 21 against a compression force of the first wire 21 on the first tension compensator 101.

When the compression force on the first tension compensator 101 is stronger with the increasing tension of the first wire 21, the first tension compensator 101 is pushed and moved back by the first wire 21. When the compression force on the first tension compensator 101 is weaker with the decreasing tension of the first wire 21 (as the first wire 21 becomes loose), the first tension compensator 101 moves forwards and pushes the first wire 21. That is, the first tension compensator 101 changes the position in response to the tension of the first wire 21.

The second tension compensator 102 is placed facing the second wire 22 and connected to the second wire 22. According to this embodiment, the second tension compensator 102 is formed in contact with the second wire 22 on the side of the second wire 22. A second spring 112 which is an elastic member is connected to the second tension compensator 102. The second spring 112 provides the second tension compensator 102 with a pushing force on the second wire 22 against a compression force of the second wire 22 on the second tension compensator 102.

When the compression force on the second tension compensator 102 is stronger with the increasing tension of the second wire 22, the second tension compensator 102 is pushed and moved back by the second wire 22. When the compression force on the second tension compensator 102 is weaker with the decreasing tension of the second wire 22 (as the second wire 22 becomes loose), the second tension compensator 102 moves forwards and pushes the second wire 22. That is, the second tension compensator 102 changes the position in response to the tension of the second wire 22.

Figure 6:
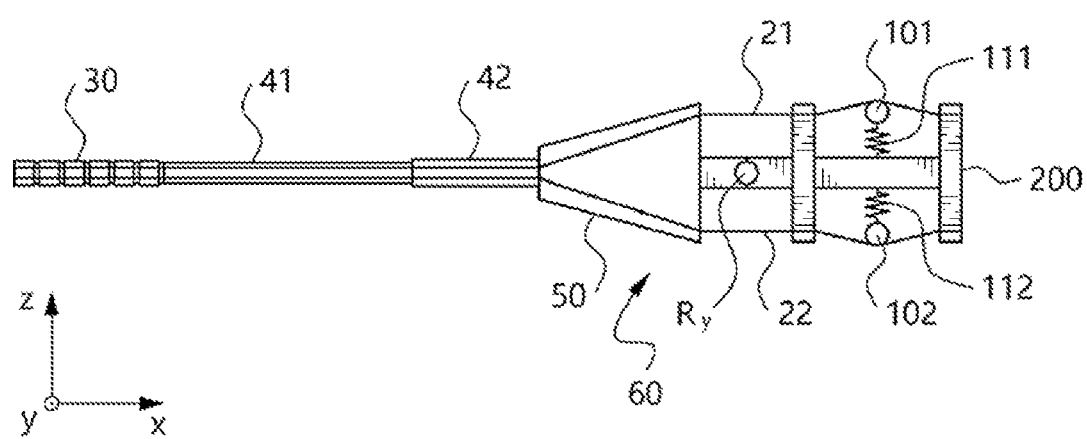
FIGS. 6 to 9 are schematic diagrams showing the configuration of the operation apparatus of FIG. 3.

As shown in FIG. 6, in the initial unsteered state of the end effector 30, the compression force of the first wire 21 on the first tension compensator 101 and the pushing force of the first spring 111 on the first tension compensator 101 are balanced, and the first wire 21 is kept tight. Likewise, the compression force of the second wire 22 on the second tension compensator 102 and the pushing force of the second spring 112 on the second tension compensator 102 are balanced, and the second wire 22 is kept tight.

In the initial state, the tension of the first wire 21 and the tension of the second wire 22 are substantially equal, and the first tension compensator 101 and the second tension compensator 102 are substantially symmetrical with respect to the lengthwise central axis of the end effector 30.

To move the surgical tool 20 closer to the surgery site, the insertion unit 11 is pushed into a cannula (not shown) that has been inserted into the body. In general, since the lumen in the body is not straight, the cannula is bent to conform to the shape of the lumen. Accordingly, as the tube 40 is inserted into the cannula, the flexible part 41 is bent to conform to the shape of the cannula.

Figure 7:
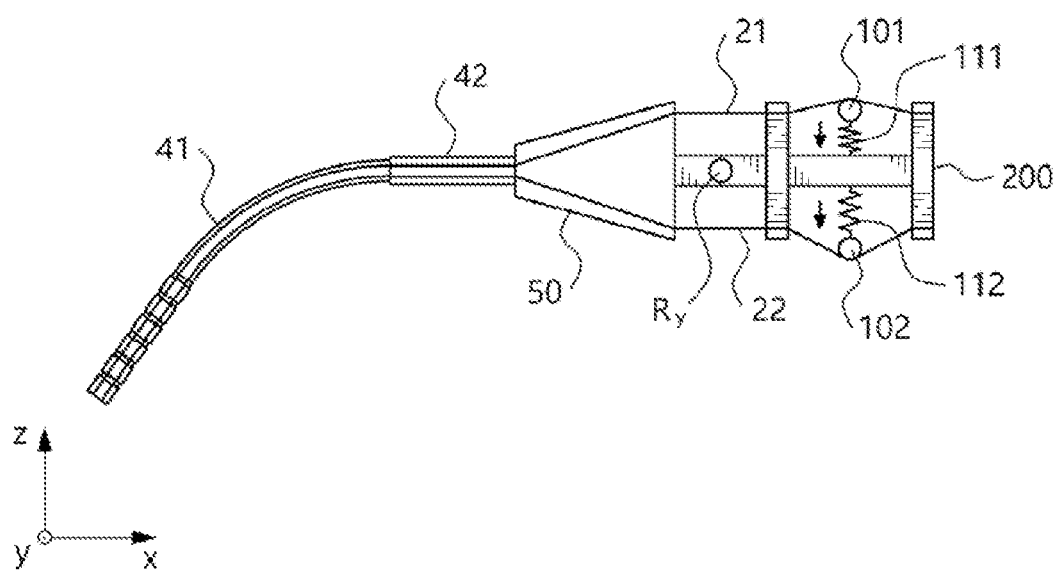

FIG. 7 shows the operation apparatus 10 with the flexible part 41 in bent state.

As shown in FIG. 7, when the flexible part 41 bends in the counterclockwise direction in FIG. 7, the first wire 21 is pulled and tension increases, and the second wire 22 becomes looser with the decreasing tension.

When the tension of the first wire 21 increases, the compression force on the first tension compensator 101 in contact on the side is stronger, and accordingly the first tension compensator 101 is pushed and moved back by the first wire 21.

In contrast, when the tension of the second wire 22 reduces, the compression force on the second tension compensator 102 in contact on the side is weaker. The second spring 112 provides a force in a direction of pushing the second wire 22, and the second tension compensator 102 advances toward the second wire 22 to keep the second wire 22 tight until the compression force of the second wire 22 and the elastic force of the second spring 112 are balanced. As described above, the tension compensator according to this embodiment changes the position in response to the tension of the connected wire to keep the corresponding connected wire tight.

As shown in FIG. 7, when the tube 40 enters the body and the tip 32 (or the surgical tool) of the end effector 30 is placed in a predetermined position, the surgery is performed by properly steering the end effector 30.

Figure 8:
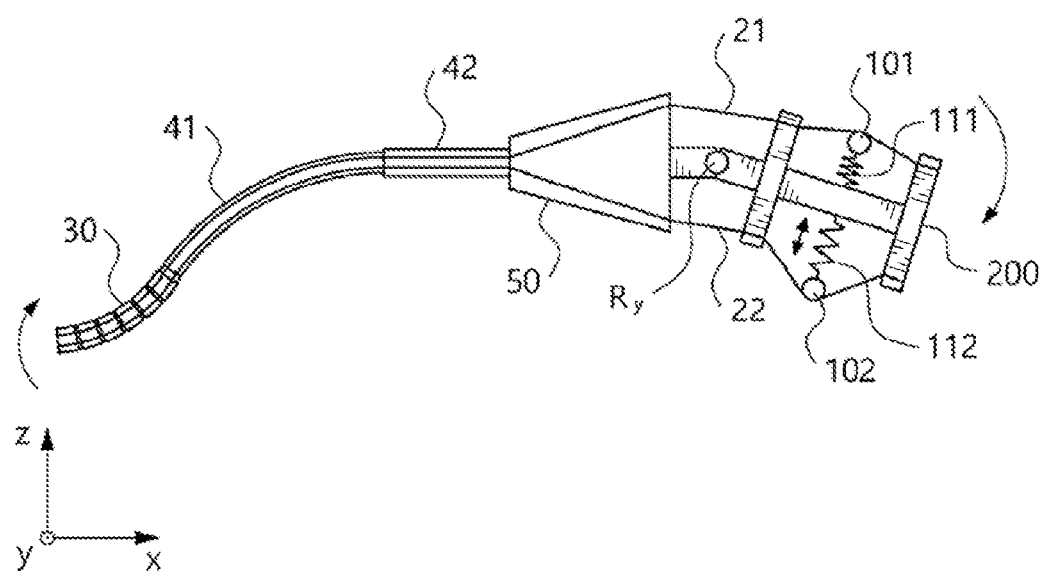

FIG. 8 shows the steering of the end effector 30 in the clockwise direction.

The operator rotates the manipulation shaft 200 around the y-axial rotation central axis Ry. By the manipulation of the manipulation shaft 200, the compression force of the first wire 21 on the first tension compensator 101 is stronger with the increasing tension of the first wire 21, and the compression force of the second wire 22 on the second tension compensator 102 is weaker with the decreasing tension of the second wire 22.

When the first tension compensator 101 and the second tension compensator 102 are in operating state in which they can freely operate, the first tension compensator 101 is pushed and moved further back by the first wire 21. Accordingly, even though the first wire 21 is pulled, the point of action of force is not fixed, so the force is not transmitted to the end effector 30. That is, until the position of the first tension compensator 101 is fixed by the complete compression of the first spring 111, the end effector 30 can be scarcely steered, namely, "backlash" may occur.

To address this phenomenon, according to this embodiment, when the wire connected to the tension compensator is pulled to steer the end effector 30, the tension compensator is in lock state in which the position is not changed.

Describing in more detail with reference to FIG. 8, when the first wire 21 is pulled back to steer the end effector 30 in the clockwise direction, the first tension compensator 101 is shifted to the lock state in which the position is not changed from the corresponding position. That is, the point of action of force on the first wire 21 is fixed. In contrast, the second tension compensator 102 is still in the operating state in which the position can be changed.

Accordingly, when the manipulation shaft 200 is rotated in the clockwise direction, in the state in which the point of action of force is fixed, the first wire 21 kept tight is pulled, and the end effector 30 is immediately steered in the clockwise direction. That is, "backlash" does not occur.

When the end effector 30 is steered in the clockwise direction, the tension of the second wire 22 changes (when the end effector 30 is only steered on the x-z plane, the tension will reduce, but as described below, when 3D steering of the end effector 30 takes place, the tension of the second wire 22 may increase). As the second tension compensator 102 is in the operating state, the second tension compensator 102 spontaneously changes the position until the compression force of the second wire 22 and the elastic force of the second spring 112 are balanced, to keep the second wire 22 tight.

Figure 9:
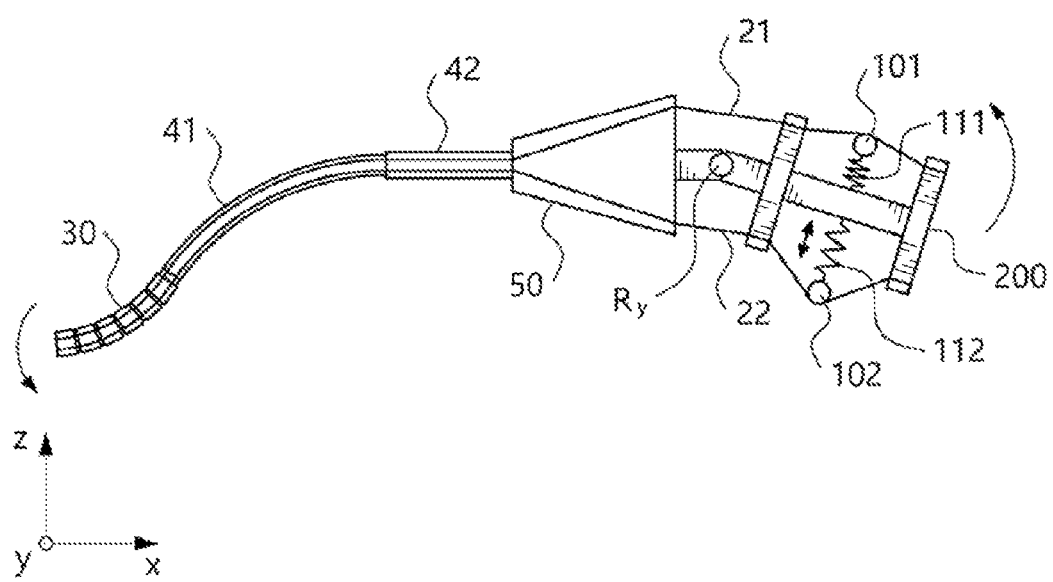

FIG. 9 shows the steering of the end effector 30 in the counterclockwise direction.

The end effector 30 may be restored from the state of FIG. 8 to the linear state, or may be further steered in the counterclockwise direction. In this instance, the operator rotates the manipulation shaft 200 in the counterclockwise direction.

When the manipulation shaft 200 is rotated in the counterclockwise direction, the second wire 22 is pulled back, and at that moment, the second tension compensator 102 is shifted to the lock state in which the position is not changed from the corresponding position. That is, the point of action of force on the second wire 22 is fixed. In contrast, the first tension compensator 101 is shifted from the lock state to the operating state in which the position can be changed.

Accordingly, when the manipulation shaft 200 is rotated in the counterclockwise direction, in the state in which the point of action of force is fixed, the second wire 22 kept tight is pulled, and the end effector 30 is substantially immediately steered in the counterclockwise direction.

When the end effector 30 is steered in the counterclockwise direction, the tension of the first wire 21 changes (when the end effector 30 is only steered on the x-z plane, the tension will reduce, but as described below, when 3D steering of the end effector 30 takes place, the tension of the first wire 21 may increase). As the first tension compensator 101 is in the operating state, the first tension compensator 101 spontaneously changes the position until the compression force of the first wire 21 and the elastic force of the first spring 111 are balanced, to keep the first wire 21 tight.

As described above, the operation apparatus 10 according to this embodiment may always keep the wire tight using the tension compensator of which the position changes in response to the tension of the wire. Accordingly, it is possible to maintain the precision of the operation apparatus 10 by preventing the wire from getting loose for some reasons, for example, when steering the end effector, when the tube bends during the insertion into the body, and when the wire is worn out.

Further, according to this embodiment, when the wire is pulled to steer the end effector, the tension compensator is shifted to the lock state in which the position is not changed, to immediately steer the end effector in response to the wire manipulation, thereby improving the workability of the operation apparatus 10.

Although this embodiment describes that the tension compensator is connected to the spring and changes the position in response to the tension of the wire, the present disclosure is not necessarily limited thereto.

The tension compensator may be any configuration that changes the shape in response to the tension of the wire, for example, an air pocket that is expanded or compressed by air pressure, or an element made of a shape-memory alloy that shrinks or expands by heat.

That is, the tension compensator according to the present disclosure is configured to keep the wire tight by changing the shape or position in response to the tension of the connected wire.

In this embodiment, the tension compensator is fixed to the compensation module and connected to the wire, but the tension compensator may be connected to the manipulation shaft.

Additionally, the tension compensator may change the position by an air cylinder or a link, rather than the spring.

When the tension compensator is configured to change the position by the spring as in this embodiment, it is possible to realize the non-powered operation apparatus 10 by the spontaneous position change of the tension compensator in response to the tension of the connected wire without a separate precise control by air or a source of power, for example, electricity.

The tension compensator may be shifted to the lock state by connecting a stopper to the manipulation shaft 200 and fixing the position of the tension compensator through a separate manipulation means, but the operation apparatus 10 according to this embodiment spontaneously shifts the tension compensator between the operating state and the lock state by the rotation of the manipulation shaft 200.

Figure 10:
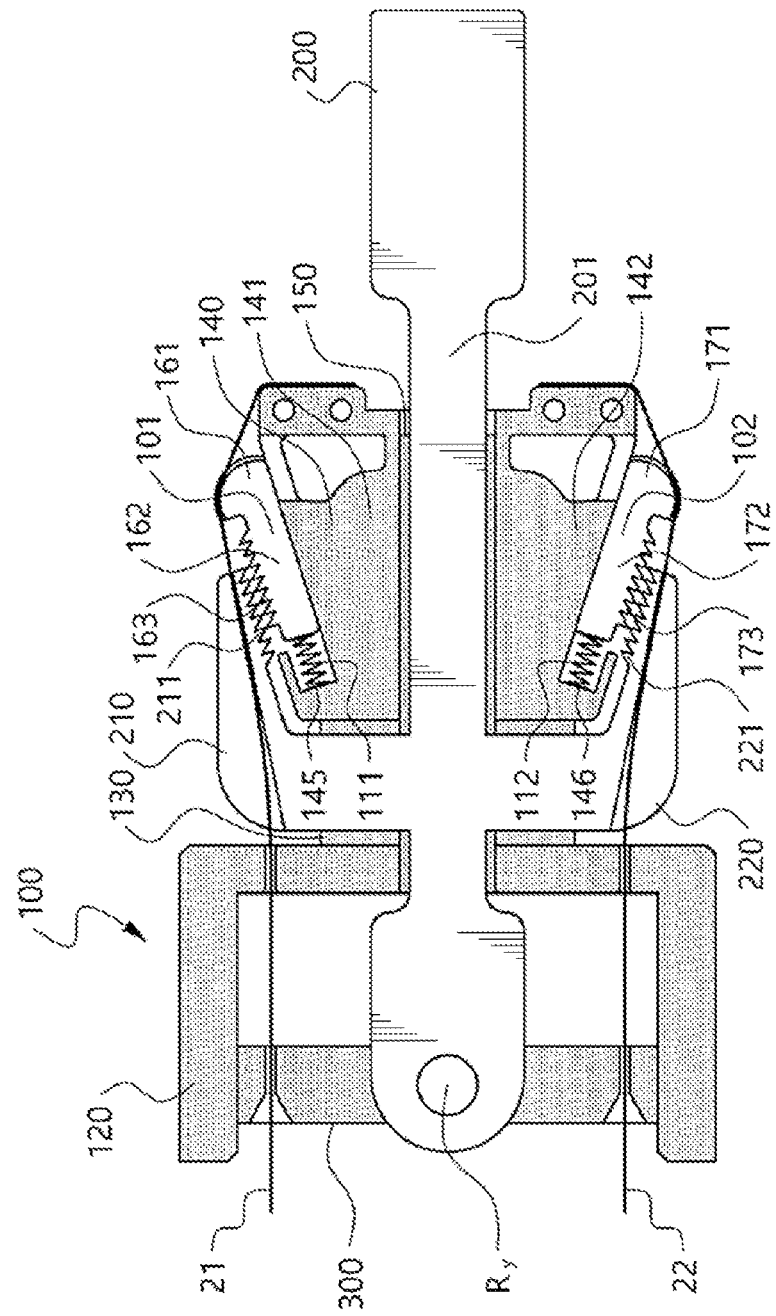
FIGS. 10 to 12 are diagrams detailing an actuation unit of the operation apparatus of FIG. 3.
Figure 11:
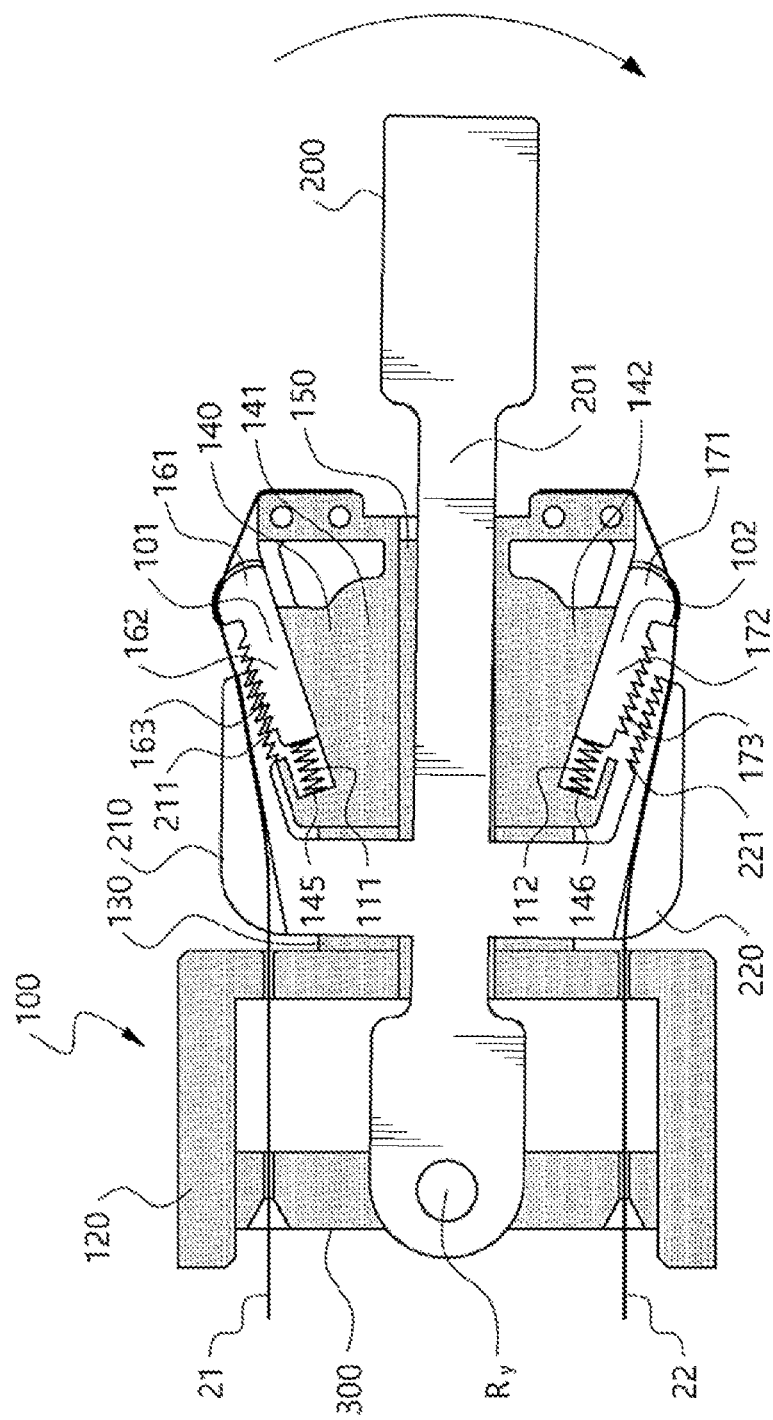
Figure 12:
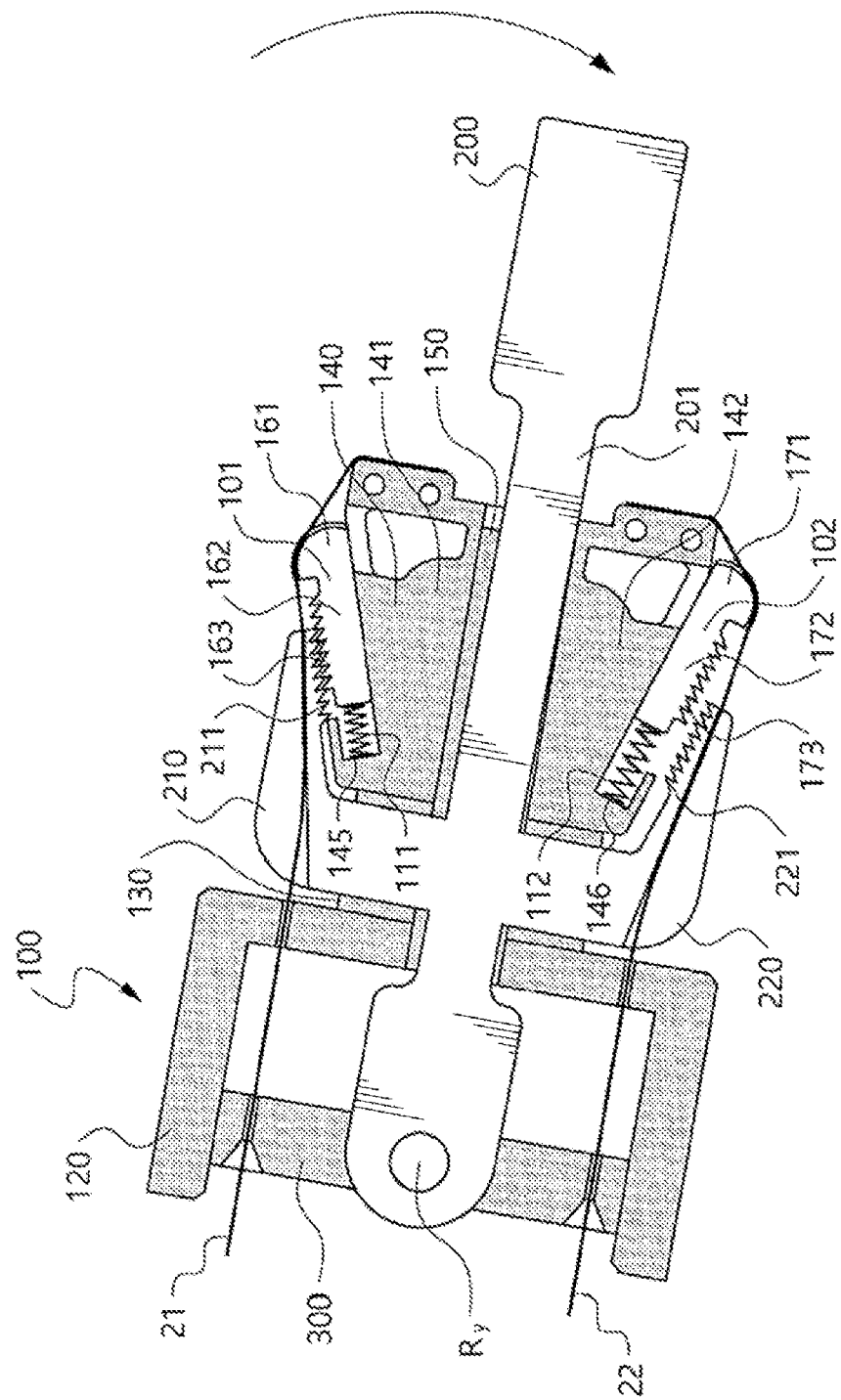

FIGS. 10 to 12 are diagrams detailing the actuation unit 60 of the operation apparatus 10.

As shown in FIG. 10, the compensation module 100 includes a rotating frame 120, a connecting frame 130 and a fixed frame 140.

The rotating frame 120 is connected to the joint module 300 and is rotatable around the y-axial rotation central axis Ry with respect to the fixture 50.

The fixed frame 140 includes a first fixed frame 141 positioned on the side of the first wire 21, and a second fixed frame 142 positioned on the side of the second wire 22 with respect to the manipulation shaft 200.

The connecting frame 130 has the front end to which the rotating frame 120 is fixed, and the rear end to which the first fixed frame 141 and the second fixed frame 142 are fixed at the same time.

The rotating frame 120, the connecting frame 130 and the fixed frame 140 are fixed together, and when the rotating frame 120 rotates around the y-axial rotation central axis Ry, the entire compensation module 100 rotates around the y-axial rotation central axis Ry.

The first fixed frame 141 has a first receiving portion 145 inclined closer to the first wire 21 as it goes toward the rear end. The first spring 111 and the first tension compensator 101 are movably inserted into the first receiving portion 145.

The first tension compensator 101 placed in the first receiving portion 145 is positioned at an angle along the inclined plane of the first receiving portion 145. The first tension compensator 101 moves the position in the diagonal direction along the inclined plane of the first receiving portion 145.

Since the compression force of the first wire 21 generally acts in the direction of inclination in which the first tension compensator 101 is positioned, the first tension compensator 101 may easily operate in response to the tension of the first wire 21.

The first tension compensator 101 includes a head 161 having a portion of an approximately cylindrical shape, and a body 162 in the shape of a plate having a height that is lower than the head 161 and a predetermined length. The body 162 has a gear 163 having gear teeth on the upper surface.

The upper surface of the first receiving portion 145 is cut to a predetermined width to expose the gear 163 of the first tension compensator 101 (see FIG. 14).

Likewise, the second fixed frame 142 has a second receiving portion 146 inclined closer to the second wire 22 as it goes toward the rear end. The second spring 112 and the second tension compensator 102 are movably inserted into the second receiving portion 146.

The second tension compensator 102 placed in the second receiving portion 146 is positioned at an angle along the inclined plane of the second receiving portion 146. The second tension compensator 102 moves the position in the diagonal direction along the inclined plane of the second receiving portion 146.

The second tension compensator 102 includes a head 171 having a portion of an approximately cylindrical shape, and a body 172 in the shape of a plate having a height that is lower than the head 171 and a predetermined length. The body 172 has a gear 173 having gear teeth on the upper surface.

The upper surface of the second receiving portion 146 is cut to a predetermined width to expose the gear 173 of the second tension compensator 102.

The manipulation shaft 200 according to this embodiment is connected to the joint module 300 and is rotatably formed around the y-axial rotation central axis Ry with respect to the fixture 50. The manipulation shaft 200 and the compensation module 100 have the same rotation central axis with respect to the fixture 50, but each of them is independently rotatable around the axial rotation central axis Ry.

The manipulation shaft 200 includes a main shaft 201, and branch shafts 210, 220 formed from the side of the main shaft 201 toward the first wire 21 and the second wire 22, respectively.

The main shaft 201 is connected to the joint module 300 rotatably around the y-axial rotation central axis Ry, and passes through the compensation module 100. The rear end of the main shaft 201 extends over the compensation module 100.

According to this embodiment, the size of an internal passage 150 of the compensation module 100 through which the main shaft 201 passes is larger than the diameter of the main shaft 201. Accordingly, the main shaft 201 is spaced apart from the internal passage 150 of the compensation module 100.

The first branch shaft 210 has an approximately "]" shape that extends toward the first wire 21 and bends toward the first tension compensator 101. A gear 211 that is engaged with the gear 163 of the first tension compensator 101 is formed on the inner surface at the end of the first branch shaft 210.

The first wire 21 passes through the rotating frame 120, and extends over the first branch shaft 210 and the head 161 of the first tension compensator 101. The rear end of the first wire 21 is fixed to the first fixed frame 141.

Likewise, the second branch shaft 220 has an approximately "]" shape that extends toward the second wire 22 and bends toward the second tension compensator 102. A gear 221 that is engaged with the gear 173 of the second tension compensator 102 is formed on the inner surface at the end of the second branch shaft 220.

The second wire 22 passes through the rotating frame 120, and extends over the second branch shaft 220 and the head 171 of the second tension compensator 102. The rear end of the second wire 22 is fixed to the second fixed frame 142.

As shown in FIG. 10, a state in which the manipulation shaft 200 does not rotate relative to the compensation module 100 (i.e., a state in which the central axis of the manipulation shaft 200 and the compensation module 100 is placed in parallel to the x axis) is referred to as a neutral state. As described in more detail below, the compensation module 100 is connected to the joint module 300 by a rotary damper, and thus is supported to prevent it from rotating itself by its self-weight in the neutral state. The neutral state of the manipulation shaft 200 is maintained by the operator holding it to prevent it from rotating downwards. However, the manipulation shaft 200 may be also connected to the joint module 300 by the rotary damper to keep it in the neutral state.

In the neutral state, the manipulation shaft 200 is not in contact with the compensation module 100 and the first tension compensator 101 and the second tension compensator 102 connected thereto.

In more detail, in the neutral state, the gear 211 of the first branch shaft 210 of the manipulation shaft 200 is in non-contact with the gear 163 of the first tension compensator 101 a little bit apart, and the gear 221 of the second branch shaft 220 is in non-contact with the gear 173 of the second tension compensator 102 a little bit apart. Accordingly, both the first tension compensator 101 and the second tension compensator 102 are brought into the operating state in which the position can change in response to the tension of the connected wires.

Although FIG. 10 shows the neutral state in which the first tension compensator 101 and the second tension compensator 102 are arranged in symmetry, the first tension compensator 101 and the second tension compensator 102 are not necessarily placed in symmetric position in the neutral state. When both the first tension compensator 101 and the second tension compensator 102 are shifted from the neutral state to the operating state, and the wire becomes loose irrespective of the active steering of the end effector 30 such as the bending of the tube 40, each tension compensator spontaneously moves the position in response to the tension change of the connected wire, to keep the wire tight (see FIG. 7).

In the neutral state, to steer the end effector 30 in a direction (the clockwise direction), the operator rotates the manipulation shaft 200 around the y-axial rotation central axis Ry.

In this instance, as the manipulation shaft 200 and the compensation module 100 are independently rotatable around the y-axial rotation central axis Ry, the compensation module 100 supported by the rotary damper is maintained and only the manipulation shaft 200 rotates the y-axial rotation central axis Ry.

As shown in FIG. 11, since the first branch shaft 210 and the first tension compensator 101 are a little bit apart from each other, when only the manipulation shaft 200 rotates around the y-axial rotation central axis Ry, the manipulation shaft 200 and the first tension compensator 101 (to be exact, the first branch shaft 210 and the first tension compensator 101) come into contact with each other almost instantaneously.

Accordingly, the gear 211 of the first branch shaft 210 and the gear 163 of the first tension compensator 101 are engaged with each other, and the first tension compensator 101 is brought into the lock state in which the position is fixed at the current position. In contrast, the second tension compensator 102 is not interfered by the manipulation shaft 200 and thus is still in the operating state.

Subsequently, as shown in FIG. 12, when the manipulation shaft 200 in contact with the first tension compensator 101 (i.e., the lock state of the first tension compensator 101) is continuously rotated in the clockwise direction, the manipulation shaft 200 applies force to the compensation module 100, and the manipulation shaft 200 and the compensation module 100 rotate around the y-axial rotation central axis Ry together.

The first wire 21 fixed to the compensation module 100 is pulled back by the rotation of the compensation module 100.

As the first tension compensator 101 is in the lock state, in the state in which the point of action of force is fixed, the first wire 21 kept tight is pulled, and the end effector 30 is immediately steered in the clockwise direction. Since the gap between the first branch shaft 210 and the first tension compensator 101 is very small compared to the total size of the operation apparatus 10, the time until the first branch shaft 210 and the first tension compensator 101 come into contact with each other is very short. Accordingly, the operator does not actually feel the time until the first branch shaft 210 and the first tension compensator 101 come into contact with each other in steering process.

In this instance, the second tension compensator 102 is in the operating state and keeps the second wire 22 tight.

In the state of FIG. 12, when the operator rotates the manipulation shaft 200 in the counterclockwise direction to steer the end effector 30 in the contrary direction (the counterclockwise direction), only the manipulation shaft 200 rotates and the second branch shaft 220 and the second tension compensator 102 come into contact with each other. Since the gap between the second branch shaft 220 and the second tension compensator 102 is also still small, when only the manipulation shaft 200 rotates around the y-axial rotation central axis Ry in the counterclockwise direction, the second branch shaft 220 and the second tension compensator 102 come into contact with each other almost instantaneously. Accordingly, the gear 221 of the second branch shaft 220 and the gear 173 of the second tension compensator 102 are engaged with each other, and the second tension compensator 102 is brought into the lock state in which the position is fixed at the current position.

In contrast, the first branch shaft 210 and the first tension compensator 101 are spontaneously released from the contact state. Accordingly, the first tension compensator 101 is brought into the operating state.

Subsequently, when the manipulation shaft 200 in contact with the second tension compensator 102 (i.e., the lock state of the second tension compensator 102) is continuously rotated in the counterclockwise direction, the manipulation shaft 200 applies force to the compensation module 100, and the manipulation shaft 200 and the compensation module 100 rotate around the y-axial rotation central axis Ry in the counterclockwise direction together.

Accordingly, the second wire 22 fixed to the compensation module 100 is pulled back by the rotation of the compensation module 100.

As the second tension compensator 102 is in the lock state, in the state in which the point of action of force is fixed, the second wire 22 kept tight is pulled, and the end effector 30 is immediately steered in the counterclockwise direction. In the same way as FIG. 12, even when the second branch shaft 220 and the second tension compensator 102 are spaced apart to the maximum extent, the gap between them is very small compared to the total size of the operation apparatus 10, so the time until the second branch shaft 220 and the second tension compensator 102 come into contact with each other is very short. Accordingly, the operator does not actually feel the time until the second branch shaft 220 and the second tension compensator 102 come into contact with each other in the steering process.

In this instance, the first tension compensator 101 is in the operating state, and keeps the first wire 21 tight.

As described above, according to this embodiment, the first tension compensator 101 and the second tension compensator 102 arranged opposite in the rotation direction of the end effector 30 are spontaneously and selectively shifted to the lock state or the operating state according to the rotation of one manipulation shaft 200. Accordingly, there is no need for a separate device or operation for manipulation of the tension compensator, thereby improving workability of the operation apparatus 10.

Hereinabove, for the understanding of the concept, the actuation unit 60 is chiefly shown on the side, and the steering trajectory of the end effector 30 on the x-z plane has been described. However, according to this embodiment, the manipulation shaft 200 accomplishes 3D motion, making it possible to simultaneously make a rotating motion around the y-axial rotation central axis Ry and a rotating motion around a z-axial rotation central axis Rz perpendicular to the y-axial rotation central axis Ry, and it is possible to steer the end effector 30 in 3D by the 3D manipulation of the manipulation shaft 200.

Figure 13:
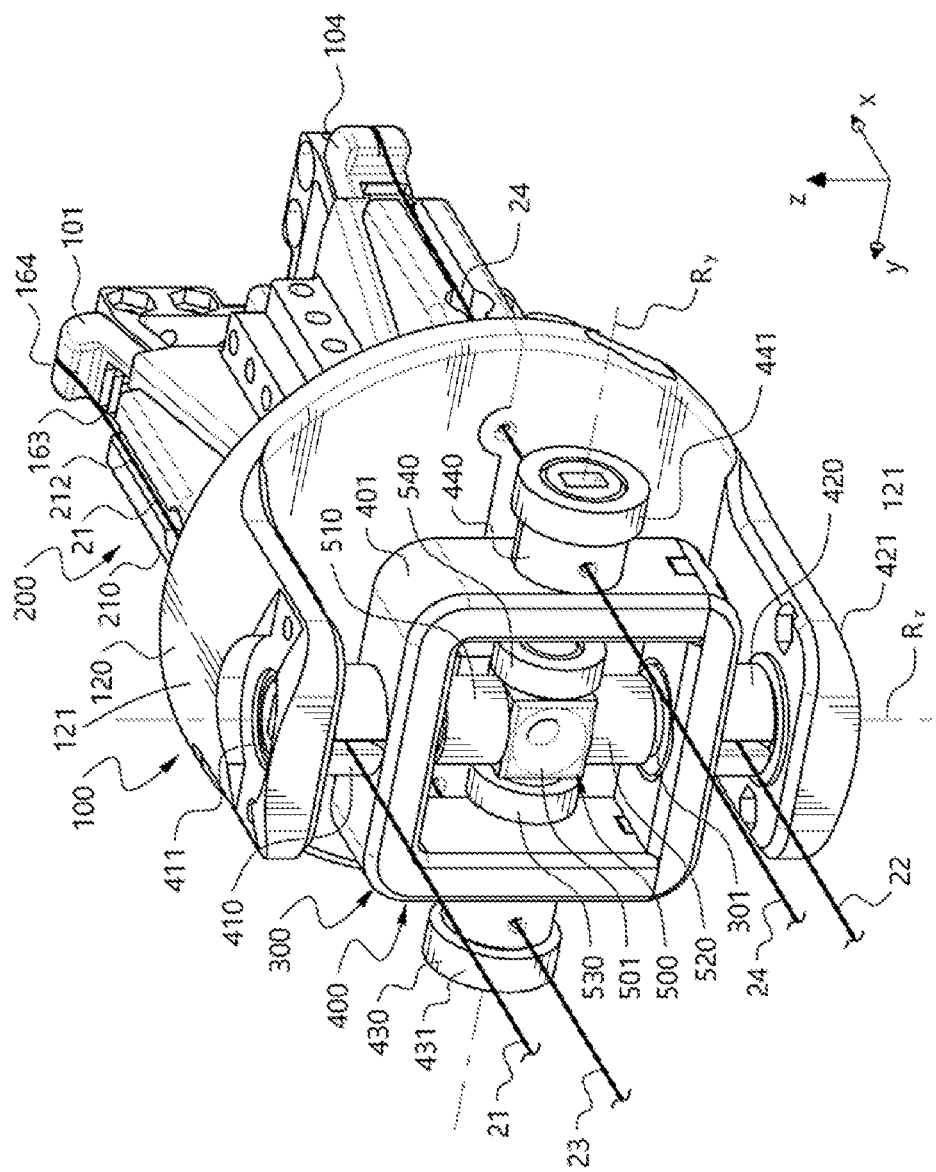
FIGS. 13 to 15 are detailed diagrams of the operation apparatus of FIG. 3, focusing on an actuation unit.
Figure 15:
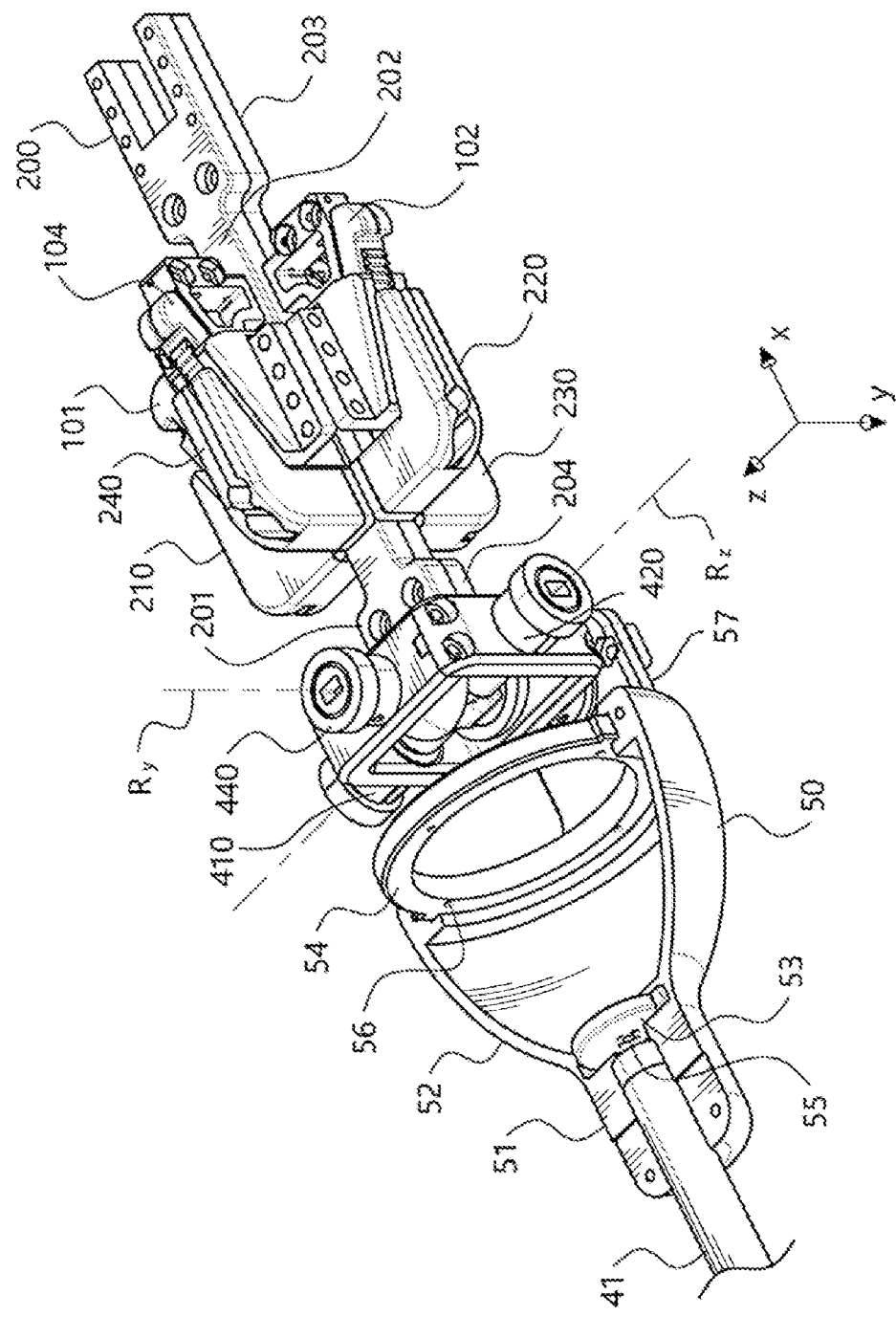

It will be described in detail with reference to FIGS. 13 to 15. FIGS. 13 to 15 are detailed diagrams of the operation apparatus 10, focusing on the actuation unit 60.

As shown in FIGS. 13 and 14, the joint module 300 has a structure including two universal joints 400, 500 to achieve 3D steering of the end effector 30.

The first universal joint 400 is a joint which allows the compensation module 100 to make a rotating motion around the y-axial rotation central axis Ry and a rotating motion around the z-axial rotation central axis Rz at the same time.

The first universal joint 400 includes a body 401 in the shape of an approximately square frame, and axes 410, 420, 430, 440 protruding from the outer surface of each side of the body 401.

The central axis of the first axis 410 and the second axis 420 arranged opposite in the z direction is concentric with the z-axial rotation central axis Rz. The central axis of the third axis 430 and the fourth axis 440 arranged opposite in the y direction is concentric with the y-axial rotation central axis Ry.

As shown in FIGS. 13 and 14, the rotating frame 120 of the compensation module 100 has an approximately "E" shape including a pair of flanges 121. The first axis 410 and the second axis 420 are rotatably inserted into the pair of flanges 121. That is, the compensation module 100 may be rotatably connected to the first axis 410 and the second axis 420, and rotate on the x-y plane with respect to the body 401 of the first universal joint 400 (rotate around the z-axial rotation central axis Rz).

Referring to FIG. 15, the fixture 50 includes a pair of flanges 57 that extend rearwards. For convenience of description, although FIG. 15 shows a half cross section of the fixture 50, the fixture 50 in complete shape has an approximately bowling pin shape that symmetrically covers the shape of the fixture 50 shown in FIG. 15.

The third axis 430 and the fourth axis 440 are rotatably inserted into the pair of flanges 57 respectively. That is, the body 401 of the first universal joint 400 may rotate on the x-z plane with respect to the fixture 50 (rotate around the y-axial rotation central axis Ry). When the body 401 rotates around the y-axial rotation central axis Ry with respect to the fixture 50, the connected compensation module 100 rotates around the y-axial rotation central axis Ry with respect to the fixture 50 together.

Meanwhile, rotary dampers 411, 421, 431, 441 are installed at the axes 410, 420, 430, 440 of the first universal joint 400 respectively to inhibit the free rotation of the connected elements 100, 50 around the axes.

The rotary dampers 411, 421, 431, 441 give a predetermined rotation resistance for the fixture 50 or the compensation module 100 to prevent the compensation module 100 from rotating itself by the gravitational force or external forces, not by the operation of the manipulation shaft 200 and keep the compensation module 100 in the neutral state with respect to the fixture 50.

The second universal joint 500 is a joint which allows the manipulation shaft 200 to make a rotating motion around the y-axial rotation central axis Ry and a rotating motion around the z-axial rotation central axis Rz at the same time.

The second universal joint 500 includes a body 501 in the shape of a square cube, and axes 510, 520, 530, 540 protruding from the outer surface of each side of the body 501.

The central axis of the first axis 510 and the second axis 520 arranged opposite in the z direction is concentric with the z-axial rotation central axis Rz. The central axis of the third axis 530 and the fourth axis 540 arranged opposite in the y direction is concentric with the y-axial rotation central axis Ry.

A head 204 surrounded by the rotating frame 120 in the main shaft 201 of the manipulation shaft 200 is rotatably connected to the third axis 530 and the fourth axis 540. Accordingly, the manipulation shaft 200 may rotate on the x-z plane with respect to the body 501 of the second universal joint 500 (rotate around the y-axial rotation central axis Ry).

The first axis 510 and the second axis 520 of the second universal joint 500 are rotatably connected to the body 401 of the first universal joint 400. The body 501 of the second universal joint 500 may rotate on the x-y plane with respect to the body 401 of the first universal joint 400 (rotate around the z-axial rotation central axis Rz). When the body 501 rotates around the z-axial rotation central axis Rz, the connected manipulation shaft 200 rotates around the z-axial rotation central axis Rz together.

Meanwhile, as shown in FIG. 13, the axes 410, 420, 430, 440 of the first universal joint 400 and the rotating frame 120 of the compensation module 100 have a wire hole through which the first wire 21, the second wire 22, the third wire 23 and the fourth wire 24 pass, respectively.

Here, the third wire 23 is a wire for steering the end effector 30 in the clockwise direction on the x-y plane, and the fourth wire 24 is a wire for steering the end effector 30 in the counterclockwise direction on the x-y plane.

As shown in FIG. 15, the four wires 21, 22, 23, 24 extending forwards with respect to the joint module 300 are fixed to the tip 32 of the end effector 30 through the fixture 50, the tube 40 and the end effector 30.

A guide member 54 and a guide member 53 are inserted into the fixture 50, the guide member 54 is formed in the shape of a ring that matches the lower end of a large diameter portion 52 of the fixture 50 and the guide member 53 is formed in the shape of a plate that matches a small diameter portion 51. The guide member 54 has four wire holes 56, and the guide member 53 also has four wire holes 55.

The four wires 21, 22, 23, 24 converge through the guide member 54 and the guide member 53 and extend into the tube 40.

Although not shown, in addition to the four wires 21, 22, 23, 24, an actuating wire (not shown) connected to the surgical tool 20 may extend into the end effector 30, the tube 40 and the fixture 50.

A hole through which the actuating wire passes may be formed at the center of the body 501 of the second universal joint 500, and a hole through which the actuating wire passes may be formed along the lengthwise center of the main shaft 201 of the manipulation shaft 200.

To reduce the size of the actuation unit 60 of the operation apparatus 10, the manipulation shaft 200 has a middle 202 having a small thickness at an overlapping area with the compensation module 100, and a tail 203 behind the middle 202 extending over the compensation module 100, to which the handle 70 is coupled.

The actuating wire is connected to an actuator 72 of the handle 70. When the operator holds a grip 71 of the handle 70 and pulls the actuator 72 with a finger, the actuating wire is pulled and the surgical tool 20 is put into operation. Otherwise, in case that the surgical tool 20 is a laser irradiator, the actuating wire may be replaced with a thin electrical wire, and the actuator 72 may be replaced with a switch.

Referring back to FIGS. 13 to 15, the four wires 21, 22, 23, 24 extending rearwards with respect to the joint module 300 extend to the compensation module 100.

As shown in FIG. 15, in addition to the first branch shaft 210 and the second branch shaft 220, the manipulation shaft 200 according to this embodiment further include a third branch shaft 230 and a fourth branch shaft 240 formed opposite in the y axis direction.

The structure of third branch shaft 230 and the fourth branch shaft 240 and the gear structure formed on them are substantially the same as the first branch shaft 210 and the second branch shaft 220 and its detailed description is omitted herein.

Additionally, in addition to the first fixed frame 141 and the second fixed frame 142, the compensation module 100 further includes a third fixed frame and a fourth fixed frame arranged opposite in the y axis direction. The third fixed frame and the fourth fixed frame are also fixed to the rotating frame 120 by the connecting frame 130. The structure of the third fixed frame and the fourth fixed frame is substantially the same as the first fixed frame 141 and the second fixed frame 142 and its detailed description is omitted herein.

A third tension compensator 103 is connected to the third fixed frame, and a fourth tension compensator 104 is connected to the fourth fixed frame.

The structure of the third tension compensator 103 and the fourth tension compensator 104 and the gear structure formed on them are substantially the same as the first tension compensator 101 and the second tension compensator 102 and its detailed description is omitted herein.

The third wire 23 passes through the rotating frame 120, and extends over the third branch shaft 230 and the head of the third tension compensator 103. The rear end of the third wire 23 is fixed to the third fixed frame.

The fourth wire 24 passes through the rotating frame 120, and extends over the fourth branch shaft 240 and the head of the fourth tension compensator 104. The rear end of the fourth wire 24 is fixed to the fourth fixed frame.

A guide groove 212 is formed on the outer surface of the first branch shaft 210 to guide the first wire 21, and the head 164 of the first tension compensator 101 also has a guide groove. The second to fourth branch shafts and the second to fourth tension compensators also have guide grooves.

The end effector 30 is steered on the x-y plane by the actuation of the third wire 23 and the fourth wire 24 by the rotation of the manipulation shaft 200 around the z-axial rotation central axis Rz.

In this instance, the third tension compensator 103 is formed in contact with the third wire 23 on the side of the third wire 23. That is, the third tension compensator 103 changes the position in response to the tension of the third wire 23.

Additionally, the fourth tension compensator 104 is formed in contact with the fourth wire 24 on the side of the fourth wire 24. That is, the fourth tension compensator 104 changes the position in response to the tension of the fourth wire 24.

When the end effector 30 is steered in the clockwise direction on the x-y plane, the third tension compensator 103 is brought into the lock state, and the fourth tension compensator 104 is brought into the operating state in which the position changes in response to the tension of the fourth wire 24. On the contrary, when the end effector 30 is steered in the counterclockwise direction on the x-y plane, the fourth tension compensator 104 is brought into the lock state, and the third tension compensator 103 is brought into the operating state in which the position changes in response to the tension of the third wire 23.

The operation of the third and fourth tension compensators for the steering of the end effector 30 on the x-y plane will be easily understood with reference to FIGS. 6 to 12 by changing y and z axes to z and y axes respectively, the y-axial rotation central axis Ry to the z-axial rotation central axis Rz, and the first tension compensator 101 and the second tension compensator 102 to the third tension compensator 103 and the fourth tension compensator respectively.

By the joint module 300 of double universal joint structure, the manipulation shaft 200 and the compensation module 100 may make a rotating motion around the y-axial rotation central axis Ry and a rotating motion around the z-axial rotation central axis Rz perpendicular to the y-axial rotation central axis Ry at the same time.

The first wire 21 and the second wire 22 are brought into operation by the rotation of the x-z plane components during 3D rotation of the manipulation shaft 200, and the third wire 23 and the fourth wire 24 are brought into operation by the rotation of the x-y plane components during 3D rotation of the manipulation shaft 200. Accordingly, it will be understood that the first tension compensator 101 and the second tension compensator 102 are selectively operated by the rotation of the x-z plane components during 3D rotation of the manipulation shaft 200, and the third tension compensator 103 and the fourth tension compensator 104 are selectively operated by the rotation of the x-y plane components during 3D rotation of the manipulation shaft 200.

According to this embodiment, as the four tension compensators automatically operate in response to the tension of the wires connected to each tension compensator, it is possible to keep all the four wires tight in the 3D steering of the end effector 30, thereby improving the manipulation performance of the operation apparatus 10.

Many modifications and variations will be obvious to those skilled in the art from the foregoing description. Accordingly, the foregoing description should be interpreted as an example, and is provided for the purpose of teaching the best mode for practicing the present disclosure to those skilled in the art. Changes may be substantially made to the structure and/or function of the present disclosure without departing from the spirit of the present disclosure.

The invention claimed is:

1. An operation apparatus for performing an operation by steering an end effector, the operation apparatus comprising:
 a wire which is connected to the end effector to steer the end effector;
 a tension compensator which is connected with the wire; and
 a manipulation shaft which is rotatably formed around a rotation central axis, wherein the manipulation shaft is perpendicular to a plane on which a steering trajectory of the end effector is placed, and pulls the wire back,
 wherein in an operating state, the tension compensator changes a shape or position of the tension compensator in response to tension of the wire to keep the wire tight, and
 when the wire is pulled to steer the end effector, the tension compensator is shifted to a lock state in which the shape or position of the tension compensator is not changed,
 wherein the tension compensator is spontaneously shifted between the operating state and the lock state by the rotation of the manipulation shaft.

2. The operation apparatus according to claim 1, wherein the tension compensator is formed in contact with the wire on a side of the wire, and changes the shape or position of the tension compensator in response to a compression force of the wire.

3. The operation apparatus according to claim 1, wherein the operation apparatus further comprises a compensation module rotatably formed around the rotation central axis, the compensation module through which the manipulation shaft passes,
  the tension compensator is fixed to the compensation module movably to change the position,
  when the manipulation shaft rotates in a direction and comes into contact with the tension compensator, the tension compensator is brought into the lock state, and
  when the manipulation shaft in contact with the tension compensator continuously rotates in the direction, the manipulation shaft and the compensation module rotate together and pull the wire back.

4. The operation apparatus according to claim 3, wherein when the manipulation shaft rotates in an opposite direction opposite to the direction on the plane, the manipulation shaft and the tension compensator are released from the contact and the tension compensator is brought into the operating state in which the position changes in response to the tension of the wire.

5. The operation apparatus according to claim 4, wherein each of the manipulation shaft and the tension compensator has a gear, and the gears are engaged with each other on a surface of the contact between the manipulation shaft and the tension compensator, and
  when the manipulation shaft and the tension compensator come into contact with each other, the gears are engaged with each other, and the tension compensator is brought into the lock state.

6. The operation apparatus according to claim 3, wherein the tension compensator is connected to the compensation module by an elastic member which is compressed or stretched depending on the tension of the wire.

7. The operation apparatus according to claim 1, wherein the operation apparatus further comprises a tube having a front end to which the end effector is coupled, the tube through which the wire connected to the end effector passes, and
  at least a portion of the tube is formed of a flexible material capable of bending.

8. The operation apparatus according to claim 1, wherein the operation apparatus further comprises
  a handle coupled to a rear end of the manipulation shaft to allow a user to hold, and
  the operation apparatus is a non-powered manually operated apparatus which ope rates by the user who holds the handle and rotates the manipulation shaft.

9. The operation apparatus according to claim 1, wherein the operation apparatus is a surgical instrument including a surgical tool which is coupled to a front end of the end effector.

10. An operation apparatus for performing an operation by steering an end effector, the operation apparatus comprising:
  a wire which is connected to the end effector to steer the end effector;
  a tension compensator which is connected with the wire; and
  a manipulation shaft which is rotatably formed around a rotation central axis, wherein the manipulation shaft is perpendicular to a plane on which a steering trajectory of the end effector is placed, and pulls the wire back,
  wherein in an operating state, the tension compensator changes a shape or position of the tension compensator in response to tension of the wire to keep the wire tight, and
  when the wire is pulled to steer the end effector, the tension compensator is shifted to a lock state in which the shape or position of the tension compensator is not changed, wherein when arbitrary x, y and z axes perpendicular to one another are defined, the operation apparatus further comprises:
  the wire for steering the end effector in a clockwise direction on an x-z plane;
  a second wire for steering the end effector in a counterclockwise direction on the x-z plane;
  the tension compensator which is connected to the wire; and
  a second tension compensator which is connected to the second wire,
  when the end effector is steered in the clockwise direction on the x-z plane, the tension compensator is brought into the lock state, and the second tension compensator is brought into the operating state in which the position changes in response to the tension of the second wire, and
  when the end effector is steered in the counterclockwise direction on the x-z plane, the second tension compensator is brought into the lock state, and the tension compensator is brought into the operating state in which the position changes in response to the tension of the wire.

11. The operation apparatus according to claim 10, wherein the operation apparatus further comprise a manipulation shaft rotatably formed around a y-axial rotation central axis; and
  a compensation module rotatably formed around the y-axial rotation central axis, the compensation module through which the manipulation shaft passes,
  each of the tension compensator and the second tension compensator is fixed to the compensation module movably to change the position, and
  the tension compensator and the second tension compensator are spontaneously and selectively shifted to the lock state or the operating state depending on a direction of rotation of the manipulation shaft relative to the compensation module.

12. The operation apparatus according to claim 11, wherein the manipulation shaft is in non-contact with the tension compensator and the second tension compensator in a neutral state in which the manipulation shaft does not rotate relative to the compensation module.

13. The operation apparatus according to claim 11, wherein the operation apparatus further comprises a third wire for steering the end effector in the clockwise direction on an x-y plane;
  a fourth wire for steering the end effector in the counterclockwise direction on the x-y plane;
  a third tension compensator which is fixed to the compensation module movably to change the position, and connected to the third wire; and
  a fourth tension compensator which is fixed to the compensation module movably to change the position, and connected to the fourth wire,
  the manipulation shaft is rotatably formed around a z-axial rotation central axis, the compensation module is rotatably formed around the z-axial rotation central axis, when the end effector is steered in the clockwise direction on the x-y plane, the third tension compensator is brought into the lock state, and the fourth tension compensator is brought into the operating state in which the position changes in response to the tension of the fourth wire, and when the end effector is steered in the counterclockwise direction on the x-y plane, the fourth tension compensator is brought into the lock state, and the third tension compensator is brought into the operating state in which the position changes in response to the tension of the third wire.

14. The operation apparatus according to claim 13, wherein 3-dimensional (3D) steering of the end effector is accomplished by 3D manipulation whereby the manipulation shaft simultaneously makes a rotating motion around the y-axial rotation central axis and a rotating motion around the z-axial rotation central axis, and the tension compensator and the second tension compensator are selectively operated by rotation of x-z plane components during the 3D rotation of the manipulation shaft, and the third tension compensator and the fourth tension compensator are selectively operated by rotation of x-y plane components during the 3D rotation of the manipulation shaft.

15. The operation apparatus according to claim 14, wherein the operation apparatus further comprises a first universal joint to allow the compensation module to simultaneously make a rotating motion around the y-axial rotation central axis and a rotating motion around the z-axial rotation central axis; and a second universal joint to allow the manipulation shaft to simultaneously make the rotating motion around the y-axial rotation central axis and the rotating motion around the z-axial rotation central axis.

16. The operation apparatus according to claim 15, wherein a rotary damper is installed at the first universal joint to give a predetermined rotation resistance for a member coupled to an axis of the first universal joint.

\* \* \* \* \*